United States Patent [19]

Manfredi et al.

[11] Patent Number: 5,105,652
[45] Date of Patent: Apr. 21, 1992

[54] COMPACT SEPARATING SYSTEM WITH SNAP-IN COLUMNS

[75] Inventors: Jose F. Manfredi, Rua Luzitana, 72 apt. A - Centro, Campinas, Sao Paulo, Brazil, 13015; Jose E. De Mendonca, Piracicaba, Brazil

[73] Assignee: Jose Felix Manfredi, Sao Paulo, Brazil

[21] Appl. No.: 548,992

[22] PCT Filed: Dec. 5, 1989

[86] PCT No.: PCT/BR89/00012
§ 371 Date: Jul. 30, 1990
§ 102(e) Date: Jul. 30, 1990

[87] PCT Pub. No.: WO90/06507
PCT Pub. Date: Jun. 14, 1990

[30] Foreign Application Priority Data

Dec. 6, 1988 [BR] Brazil .................................. 8806499
Dec. 12, 1988 [BR] Brazil .................................. 8806649

[51] Int. Cl.5 .......................................... G01N 30/54
[52] U.S. Cl. .............................. 73/23.250; 73/23.420
[58] Field of Search .................. 73/23.25, 19.02, 23.42

[56] References Cited

U.S. PATENT DOCUMENTS

| | | | |
|---|---|---|---|
| 3,285,055 | 11/1966 | Reinecke | 73/23.25 |
| 3,305,000 | 2/1967 | Bullen et al. | 73/23.25 X |
| 3,403,545 | 10/1968 | Carter | 73/23.25 |
| 3,440,397 | 4/1969 | Vesper et al. | 73/23.25 X |
| 3,996,017 | 12/1976 | Kaiser | 73/23.35 X |
| 4,044,593 | 8/1977 | Haruki et al. | 73/23.25 |
| 4,057,998 | 11/1977 | Moreaux | 73/23.25 |
| 4,096,908 | 6/1978 | Lamy | 73/23.25 X |

Primary Examiner—Hezron E. Williams
Assistant Examiner—Joseph W. Roskos
Attorney, Agent, or Firm—Beveridge, DeGrandi & Weilacher

[57] ABSTRACT

A fluid separation system applicable to gas chromatography includes a separating column in the form of a coiled tube in a thermally insulated enclosure. The ends of the coiled tube are connected by snap-action couplings to the outlet of an injector and the inlet of a detector which generates an electrical signal corresponding to the component of the fluid being separated. Snap action couplings also connect the thermally insulated enclosure to a thermal control system which circulates a heat exchange fluid to define the temperature in the enclosure.

17 Claims, 1 Drawing Sheet

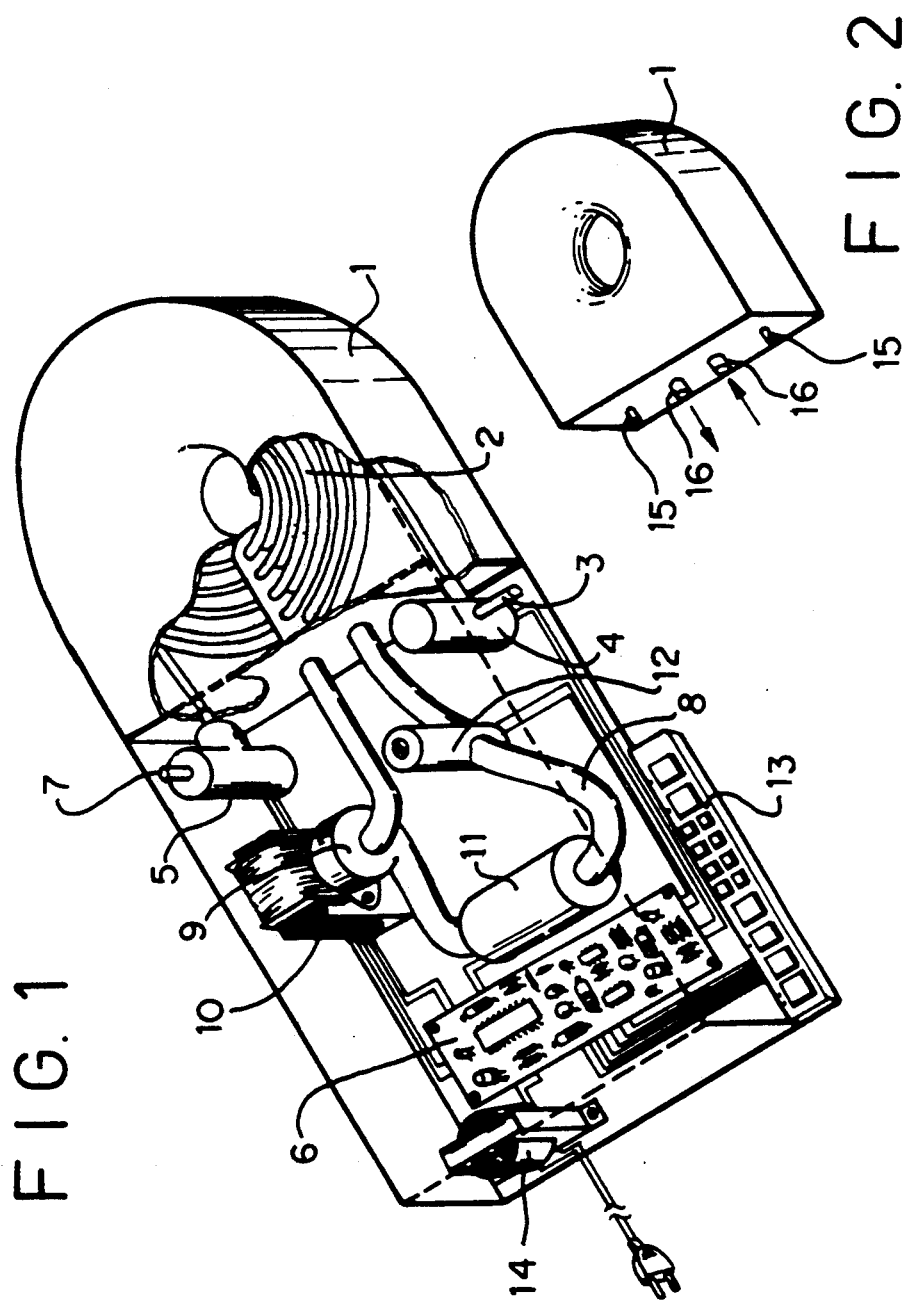

COMPACT SEPARATING SYSTEM WITH SNAP-IN COLUMNS

FIELD OF APPLICATION

The instrument herein described is proposed for application in chemical analysis involving separation techniques such as in gas chromatography.

TECHNICAL BACKGROUND

The systems presently in use for chromatographic analysis, using gases or supercritical fluids as the mobile phase, utilize large ovens, with volumes on the order of various cubic decimeters, sufficient to accomodate one or more columns and to adequately control the temperature, or the programing of the temperature, using confined hot air. The columns are installed using different types of threaded connectors normally containing appropriate ferrules to avoid fluid leakage.

A complete description of such equipment can be found in the literature on chromatography. We suggest the book "Modern Practice of Gas Chromatography", R. L. Grob, ed., $2^{nd}$ edition, John Wiley and Sons, New York, 1985.

GENERAL DESCRIPTION OF THE INVENTION

Systems built in accordance with this invention have two main portions. One of them is represented by a replaceable capsule which contains an analytical column through which circulates a temperature-controlling fluid, the analytical column is protected against mechanical damage by the capsule container. The small volume of the capsule container permits better temperature control and more rapid and reliable temperature programming when in use. The attachment, and removal, of the column capsule from the instrument is carried out manually, without the need of tools, using planar or spherical connectors without threads. Two connections are for the entrance and exit of the analytical fluid. Two other connections permit the circulation of the temperature control fluid.

Within the other portion of the system there is a unit which activates the circulation of this fluid, which may be heated or cooled, and for control and monitoring of the temperature, controlled through appropriate electronic circuitry. The instrument also has means to permit the entrance of analytical fluid, sample injection into this analytical fluid, and a detector for the partially or completely separated original components, whose signal is transferred, by appropriate electrical connections to an electronic amplifier, for simultaneous or subsequent display.

DESCRIPTION OF THE DRAWINGS

An example of the separation system of the invention is illustrated in which:

FIG. 1 is a partially broken away perspective view of one preferred embodiment of the apparatus of the present invention; and FIG. 2 is a perspective view of the column capsule, showing its coupling means.

FIG. 1 shows a proposed instrument coupled to the column capsule (1) which contains the analytical column (2). The analytical fluid, such as a gas, enters the instrument through opening (3). The sample is introduced into the fluid stream through the injector (4) which has its own independent temperature control system.

The sample is completely or partially separated during its passage through the column and exits from the column into a detector (5), which indicates the presence of the separated components by means of an electronic signal that is received, processed and then registered and in storage means stored (6). After passing through the detector the analytical fluid and sample exit through opening (7).

The temperature control fluid circulates through ducts (8), propelled by a pump (9) activated by a motor (10). The heating or cooling of this fluid is carried out in a small chamber (11) equipped with a heating element, such as a resistor, and with a system to exchange heat with external atmosphere, by convection or forced air circulation. Control of temperature is done by means of appropriate electronic circuitry and monitored by a thermometric system, such as a thermocouple (12).

The operation parameters are controlled and monitored by use of a small panel (13) and appropriate electronics and the resulting information is displayed and/or stored. The equipment operates in alternating current (110/220 volts and 50/60 hertz) with an internal transformer (14).

FIG. 2 shows details of the connections between the column capsule and the instrument with the column ends (15), and the temperature control fluid fittings (16).

CONSTRUCTION OF THE INSTRUMENT

The column, usually in the form of a capillary tube, is made of glass, fused silica, or metal, with lengths from few centimeters to many meters, and has usually received special treatment on the inner surface to permit sample separation to occur. The column is supported within the capsule in such a manner as to permit easy circulation of the temperature controlling fluid.

The capsule is made of metal or other material that has a good resistance against the working limit of temperature, which is about 500° C. for some columns and is expected to be higher as column technology improves. The capsule inner wall is made reflective and the external one is coated with a thermally insulating cover.

The instrument container itself is made of metal or a mechanically resistant plastic. The temperature controlling fluid is contained in a thermally insulated metal tubing loop and the connections between the capsule and the instrument itself are made of tantallum, glass or quartz, with highly polished, smooth surfaces.

The injector and detector may be anyone of many already available commercially and will be incorporated into the instrument as required. The electronic control of the whole system is carried out using an already available broad from a microcomputer. The results are displayed in an external device, not shown in the drawing, that can be a screen or a printer/plotter recorder.

APPLICATIONS

The instrument may be used in any determination which involves separation and qualitative/quantitative analysis of gases or volatile species in a fluid stream, either in a laboratory environment or directly coupled to a process line.

We claim:

1. Fluid separation system, particularly applicable to gas chromatography, comprising:

injector means having a fluid inlet and a fluid outlet;
detector means having a fluid inlet and a fluid outlet, capable of generating an electric signal corresponding to the components of the fluid being separated;
an electrical output connected to the detector;
thermal control means operable to circulate a heat exchange fluid; and
a separable, thermally insulated portion within which is disposed a first tube which is coiled and has its ends connectable respectively to said injector's outlet and to said detector's inlet through snap-action couplings; and, a second tube being connectable to said thermal control means and connectable to said thermally insulated portion through snap-action couplings.

2. System according to claim 1, wherein said couplings are spherical connectors.

3. System according to claim 1, wherein said couplings are planar connectors.

4. System according to claim 1, wherein said thermal control means includes heating means and thermometric means, said heating means comprising a resistor and a chamber, wherein said resistor is disposed within said chamber, and wherein said thermally insulated portion is also mechanically insulated.

5. System according to claim 4, wherein said thermal control means includes a pump.

6. System according to claim 5, further comprising storage means for storing the electrical signals provided by said detector means.

7. System according to claim 6, further comprising display means connected to said detector means and data input means connected to said thermal control means.

8. System according to claim 7, wherein said thermal control means further includes cooling means.

9. Fluid separation system, particularly applicable to gas chromatography, comprising:
injector means having a fluid inlet and a fluid outlet;
detector means having a fluid inlet and a fluid outlet, capable of generating an electrical signal corresponding to the components of the fluid being separated;
an electrical output connected to the detector;
thermal control means operable to circulate a heat exchange fluid;
wherein said fluid separation system also comprises a separable, thermally insulated enclosure, within which is disposed a coiled tube, the ends of which are co-operable respectively with said injector's outlet and said detector's inlet, the temperature within said enclosure being defined by said heat exchange fluid.

10. System according to claim 9, wherein said coiled tube is connectable to said injector and to said detector through snap-action couplings.

11. System according to claim 10, wherein said couplings are spherical connectors.

12. System according to claim 10, wherein said couplings are planar connectors.

13. System according to claim 10, further comprising a second tube connected to said thermal control means and connectable through snap-action couplings to said thermally insulated enclosure, which is also mechanically insulated.

14. System according to claim 13, wherein said thermal control means includes heating means and thermometric means, said heating means comprising a resistor and a chamber, wherein said resistor is disposed within said chamber.

15. System according to claim 14, further comprising storage means for storing electrical signals provided by said detector means.

16. System according to claim 15, further comprising display means connected to said detector means and data input means connected to said thermal control means.

17. System according to claim 16, wherein said thermal control means further comprises cooling means and a pump.

* * * * *